United States Patent [19]
Puddu

[11] Patent Number: 5,749,875
[45] Date of Patent: May 12, 1998

[54] BONE PLATE SYSTEM FOR PROXIMAL TIBIAL OSTEOTOMY

[75] Inventor: Giancarlo Puddu, Rome, Italy

[73] Assignee: Arthrex, Inc., Naples, Fla.

[21] Appl. No.: 783,203

[22] Filed: Jan. 14, 1997

Related U.S. Application Data

[62] Division of Ser. No. 440,306, Mar. 24, 1995, Pat. No. 5,620,448.

[51] Int. Cl.⁶ .................................................. A61B 17/58
[52] U.S. Cl. ................................ 606/87; 606/86; 606/69; 606/72
[58] Field of Search ..................... 606/82–87, 69–71, 606/73; 30/304, 305, 315

[56] References Cited

U.S. PATENT DOCUMENTS

| | | | |
|---|---|---|---|
| 1,769,525 | 7/1930 | Maness | 30/304 |
| 4,472,879 | 9/1984 | Sizemore, Jr. | 30/304 |
| 4,793,335 | 12/1988 | Frey et al. | 606/73 |
| 4,969,267 | 11/1990 | Anenberg | 30/304 |
| 5,026,385 | 6/1991 | Schutte et al. | 30/304 |

*Primary Examiner*—Michael Buiz
*Assistant Examiner*—Daphna Shai
*Attorney, Agent, or Firm*—Ostrolenk, Faber, Gerb & Soffen, LLP

[57] ABSTRACT

A system for performing proximal tibial or femoral osteotomies. The system includes a plurality of bone plates of various sizes, and a calibrated wedge tool for opening a resected tibial wedge and determining the size plate to use in the osteotomy.

12 Claims, 7 Drawing Sheets

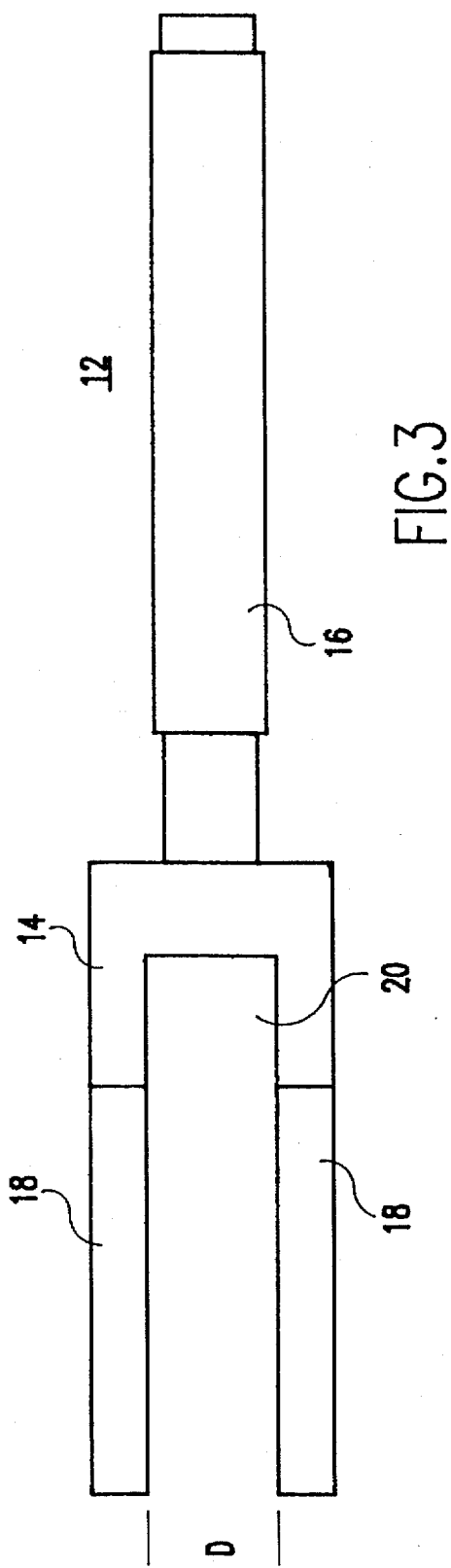
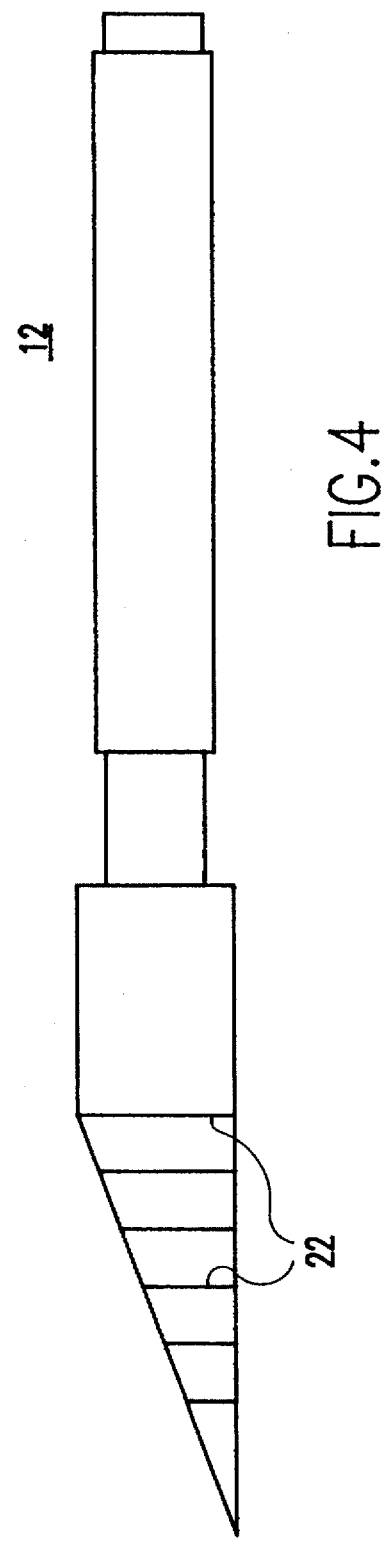

BONE PLATE SYSTEM FOR PROXIMAL TIBIAL OSTEOTOMY

This is a division of application Ser. No. 08/440,306, filed Mar. 24, 1995 now U.S. Pat. No. 5,620,448.

BACKGROUND OF THE INVENTION

1. Field of the Invention

The present invention relates to a system for performing proximal tibial osteotomies.

2. Description of the Related Art

Tibial osteotomies are performed to correct certain deformities. High tibial osteotomies (HTO) are indicated by early, medial joint-space narrowing, by early arthritis in patients who have had previous medial meniscectomy, or following rupture of the anterior cruciate ligament (ACL) in patients with pre-existing varus deformity, for example.

There are two schools of thought regarding osteotomy methods: the closing wedge method, and the opening wedge method. In the closing wedge method, removal of a bone wedge creates an angled gap in the bone. Part of the bone is left as a hinge at the apex of the angle. The hinge allows the gap to narrow, and the bone material on either side of the closed gap joins together.

In the opening wedge method, a cut is made across the bone. Part of the bone is left as a hinge, as in the closing wedge method. In contrast to the closing wedge method, however, the hinge allows the cut gap to open. The open wedge is filled with graft material.

The two methods are performed on opposite sides of the bone to give equivalent results. For example, when a given deformity would be corrected by performing the opening-wedge procedure on the medial side of a bone, an equivalent closing-wedge correction would be performed laterally.

The closing wedge method is the current standard, although several disadvantages are associated with the technique. The most significant disadvantages of the closing wedge method are: (i) disruption of the tibial-femoral joint; (ii) possible damage to neurovascular structures; and, (iii) disruption of the medial cortex, resulting in instability and nonunion between the upper and lower bone because of possible soft tissue interference. It is also difficult to compute the correct amount of bone to remove, and, therefore, several extra cuts may be required.

The opening wedge technique avoids or limits many of the disadvantages associated with the closing wedge method. Additionally, the medial, open-wedge HTO has the following advantages over the closed, lateral-wedge HTO: (i) speed; (ii) simplicity; (iii) ability to quickly change angle at any time during the procedure; and (iv) no fibular osteotomy is required. Nevertheless, only a few surgeons are currently using the opening wedge procedure. This is most likely due to a lack of proper instrumentation. Thus, a need exists for proper instrumentation to perform the opening wedge technique.

SUMMARY OF THE INVENTION

The present invention overcomes the disadvantages of the prior art and fulfills the above-described need by providing a bone plate system for performing the opening wedge osteotomy technique. The bone plate system of the present invention includes two basic components: a forked-wedge tool for opening the wedge, and a set of bone plates for maintaining the wedge opening. The tool and the bone plates are designed to allow bone plate insertion while the tool is in place.

Each bone plate includes a distal projection having a length and a depth. The depth of the projection preferably is 4 mm. The system preferably includes five bone plates, and the length of the projection on each bone plate is 5 mm, 7.5 mm, 10 mm, 12.5 mm and 15 mm, respectively.

According to a preferred embodiment of the invention, each of the ends of the bone plates has a screw hole. The holes are counterbored to receive bone screws for securing the plates to the tibia, and the proximal side of the plate is curved distally to conform with the tibial surface.

The wedge tool is forked at a distal end, and has a handle at a proximal end. The two ends preferably share a common, longitudinal axis. The fork is wedge-shaped and preferably includes two prongs having a linearly-tapered thickness. The two prongs are separated from each other by a distance greater than the width of the bone plates. Preferably, the tapered thickness of the wedge is calibrated in relation to the length of the bone plate projections.

The present invention also provides a method of correcting a deformity by performing an osteotomy using the aforementioned bone plates and forked-wedge tool. A tibial osteotomy is performed according to a preferred method of the present invention by forming an incision over the tibia, and resecting the tibia from the medial side toward the lateral side so as to leave a bony hinge on the lateral side.

Preferably, a pin is inserted into the tibia prior to the resection, from the medial side to the lateral side, to guide the tibial resectioning. Insertion of the pin is performed under fluoroscopic control. The pin preferably is a 4 mm Steinmann pin that is placed from the medial side to the lateral side following a path beginning approximately 3 to 5 centimeters below a tibial-femoral joint line on the medial side of the tibia, and ending at a point approximately 1 to 2 centimeters below the joint line laterally on the tibia.

The resection is wedged open with the tool by inserting the tapered prongs to a depth at which the deformity is corrected. The calibrated wedge enables the surgeon to determine what size spacer is needed and to pick the appropriate bone plate. This helps to prevent disruption of the tibial-femoral joint.

Once the correct opening is established by insertion of the wedge tool, a bone plate is selected which has a projection length equal to the thickness of the tool at the deformity-correcting depth. The selected bone plate is then placed between the two prongs of the tool, and the projection of the bone plate is inserted distally into the resection opening.

With the bone plate inserted in the resection opening, the screw holes are located above and below the resection opening. Bone screws are inserted through the screw holes to secure the plate to the tibia. The forked tool is removed, and autologous bone is packed into the resection.

The bone plate, in conjunction with the autologous-bone graft filler, provides an effective means of eliminating the deformity. Further, the procedure is performed on the medial side, thus making it easier, faster and more reproducible than previous methods.

Other features and advantages of the present invention will become apparent from the following description of the invention with reference to the accompanying drawings.

BRIEF DESCRIPTION OF THE DRAWINGS

FIG. 3 is a plan view of the forked insertion tool according to a preferred embodiment of the present invention.

FIG. 4 is an elevation of the forked insertion tool according to a preferred embodiment of the present invention.

DETAILED DESCRIPTION OF THE PREFERRED EMBODIMENTS

Figure 1:
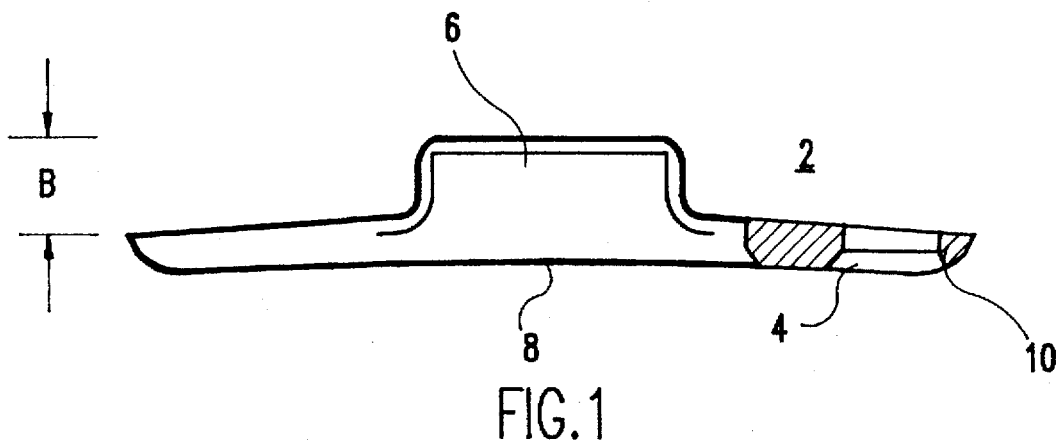
FIG. 1 is an elevation of a bone plate according to the present invention.
Figure 2:
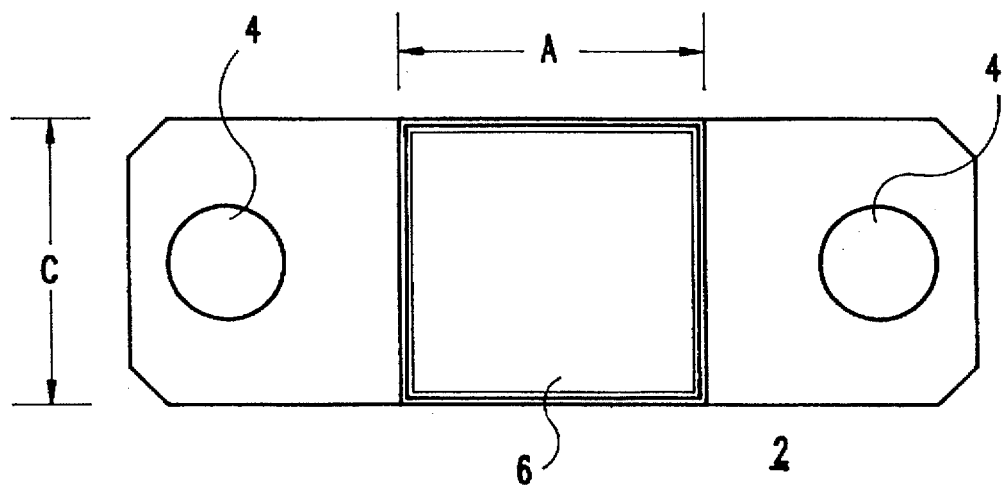
FIG. 2 is a plan view of a bone plate according to the present invention.

Referring first to FIGS. 1 and 2, the bone plate system of the present invention consists of a set of five stainless steel plates 2 each including two holes 4 at opposite ends for receiving AO cortical or cancellous screws, and a projection 6. The plates have projections of various lengths A (5 mm, 7.5 mm, 10 mm, 12.5 mm, and 15 mm). The correct plate is selected such that projection 6 interposes into the osteotomy in accordance with the degree of axial correction desired by the surgeon. The height B of the projection is preferably 4 mm. Once the plate is synthesized at the site, the projection prevents the osteotomy from losing the obtained correction.

The bone plate has a proximal surface 8 which preferably is curved as shown in FIG. 1 to conform generally with the surface of the tibia. Each of the two holes 4 has a tapered counterbore 10 for receiving the head of a bone screw. Preferably, a cancellous screw is used in the proximal hole, and a cortical screw is used in the distal hole. Bone plate 2 has a width C that is sized to be accommodated by an insertion tool, described below.

Referring now to FIGS. 3 and 4, the system further includes a forked, wedge-shaped insertion tool 12. Tool 12 includes a head 14 and a handle 16, preferably made of stainless steel or other surgically acceptable material.

Tool head 14 includes two prongs 18 having smooth, linearly-tapered faces. Prongs 18 define an opening having a width D which is greater than the width C of bone plate 2. The opening extends into recess 20 which is disposed proximally to the end of the inclined faces. Prongs 18 are calibrated in millimetric graduations 22, which allows the surgeon to obtain the desired correction and easily determine the correct size bone plate.

Surgical Technique

The method of performing opening wedge osteotomy in accordance with the present invention will now be described. Prior to the surgery, full length standing AP and lateral x-rays are obtained and correction angles are measured and marked on the x-rays to determine the appropriate size plate needed. A routine arthroscopy is performed and general joint debridement is carried out. Any osteochondral defects are penetrated using Arthrex Chondro picks (available from Arthrex, Inc. of Naples, Fla.) and a standard micro-fracture technique. A 4 cm. skin incision is made over the pes anserinus insertion and the medial collateral ligament is incised.

The following surgical steps are then performed:

1. The patient is prepped and draped in the usual fashion, keeping in mind that intra-operative fluoroscopy will be used on the lower extremity. Prophylactic antibiotics are given at the surgeon's discretion.

2. An antero-medial incision is made over the tibia 3 to 5 centimeters below the joint line.

Figure 5:
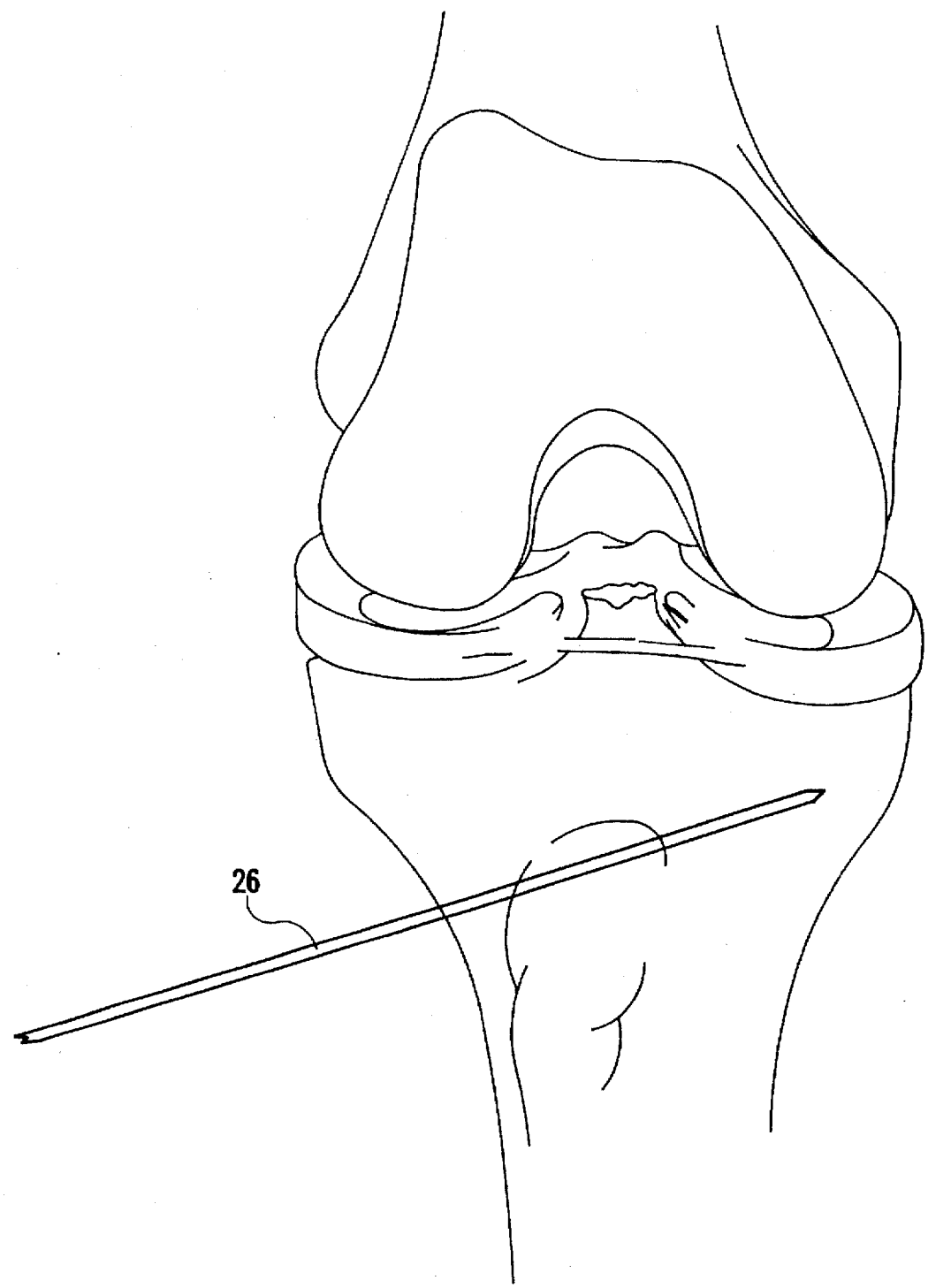
FIG. 5 is a schematic representation of the guide-pin insertion step in the method of the present invention.

3. Referring to FIG. 5, a 4 mm Steinmann pin 26, which will act as an orientation marker, is drilled from medial to lateral starting at approximately 5 mm superior and 2.5–3.0 cm medial to the tibial tubercle and exiting approximately 1 cm inferior to the lateral tibial plateau.

Figure 6:
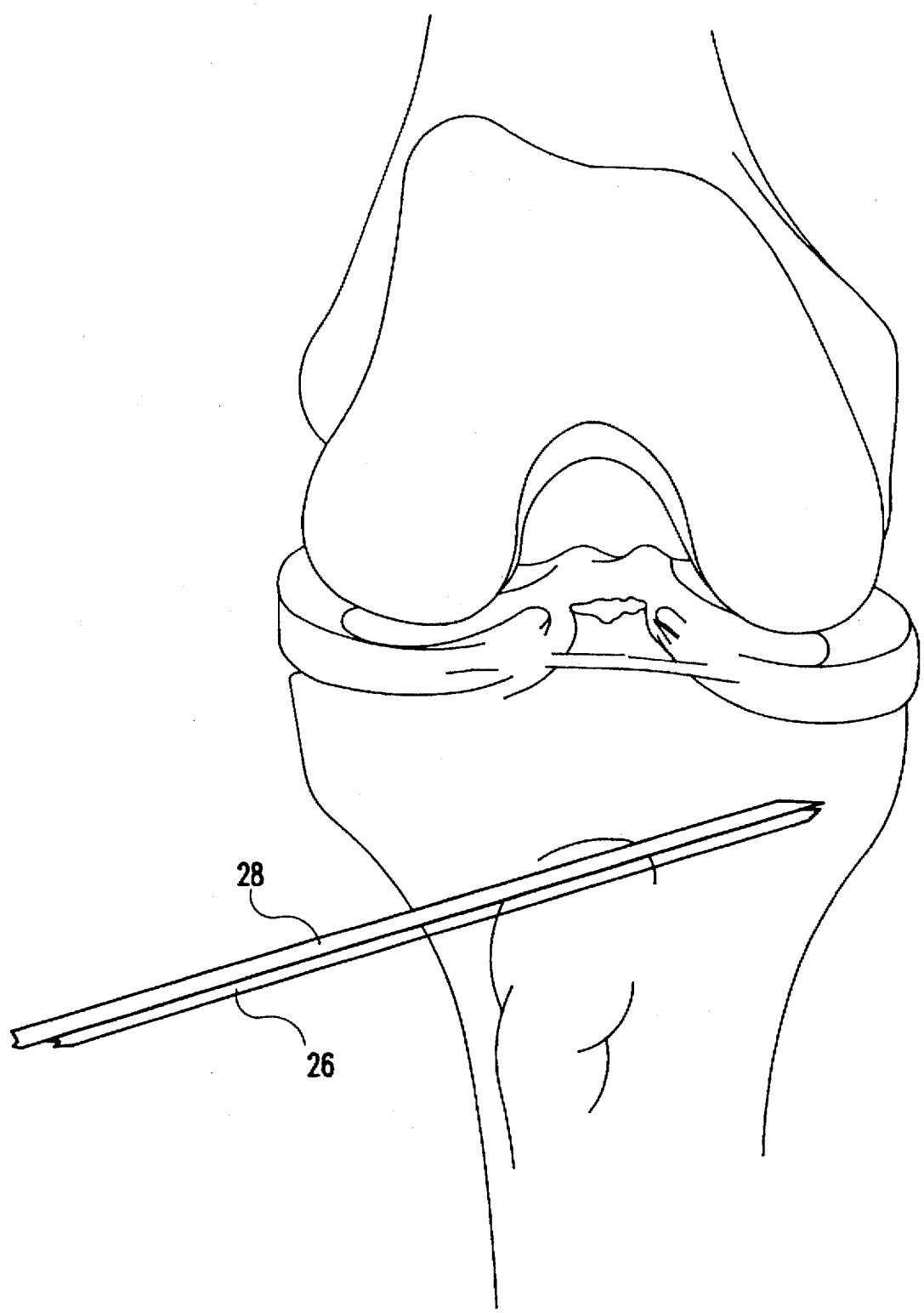
FIG. 6 is a schematic representation of the resecting step in the method of the present invention.

4. Using a wide, thin osteotome 28, as shown schematically in FIG. 6, the tibia is resected along the same plane as the previously placed Steinmann pin, using the pin as a guide, taking care to leave a bony hinge on the lateral side. An oscillating saw may be used to resect the tibial cortex superior to the marking guide pin in the tibial tubercle. The wedge is then completed using the osteotome. The lateral cortical wall is not resected but is left intact to act as a hinge for the medial osteotomy. Pin 26 is removed after completing the osteotomy.

Figure 7:
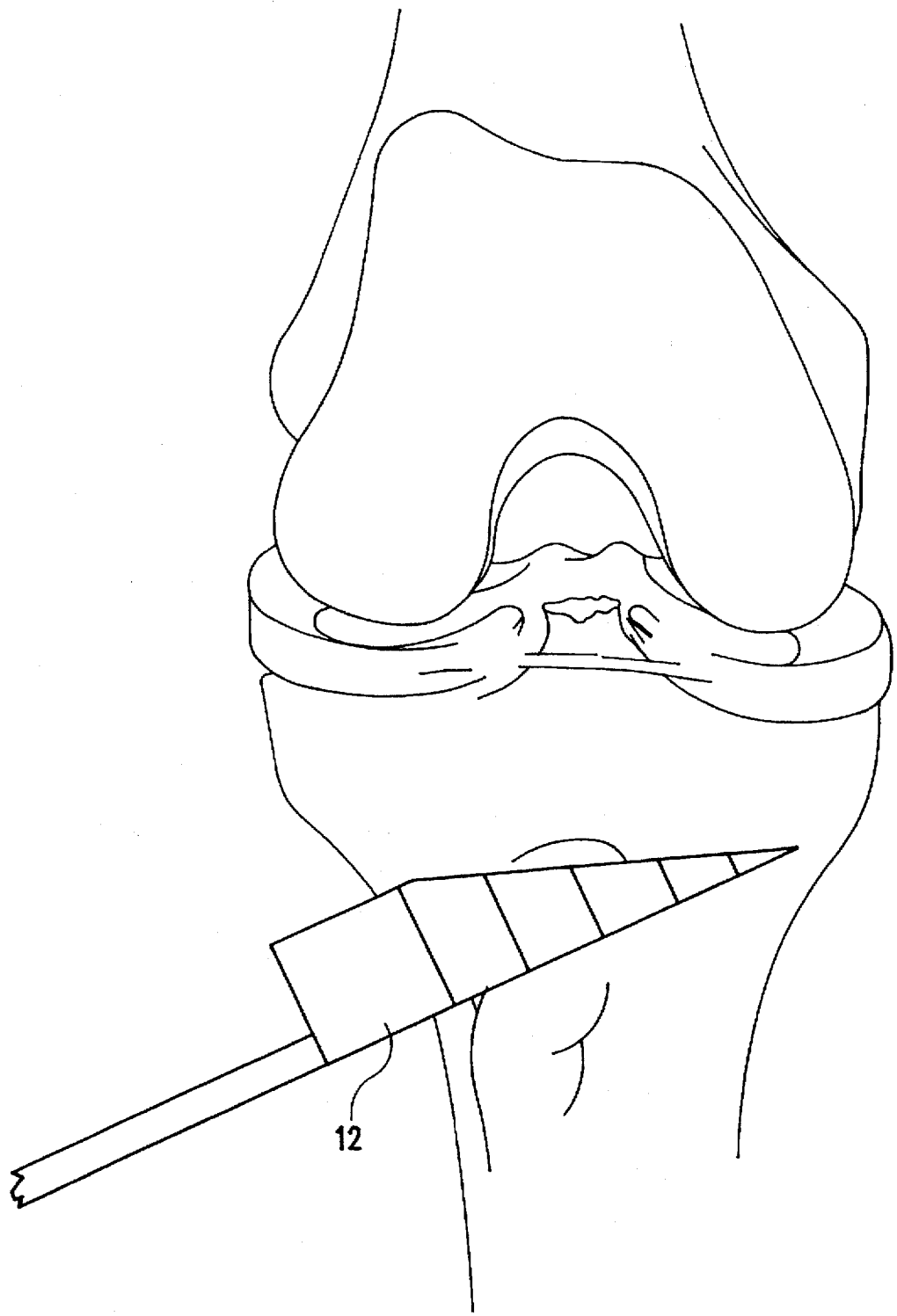
FIG. 7 is a schematic representation of the forked wedge tool insertion step in the method of the present invention.

5. The osteotomy site is then carefully opened using the calibrated forked wedge tool 12. See FIG. 7. The medial open wedge is created by inserting the calibrated wedge tool in the opening to the desired depth to create the required medial opening. The forked wedge tool 12 is inserted into the osteotomy until the deformity is corrected. Calibrations on the side of the tool make measuring the width of the osteotomy quick and easy. Once the necessary correction angle has been obtained, the osteotomy plate containing the appropriate spacer is selected from the implant tray.

Figure 8:
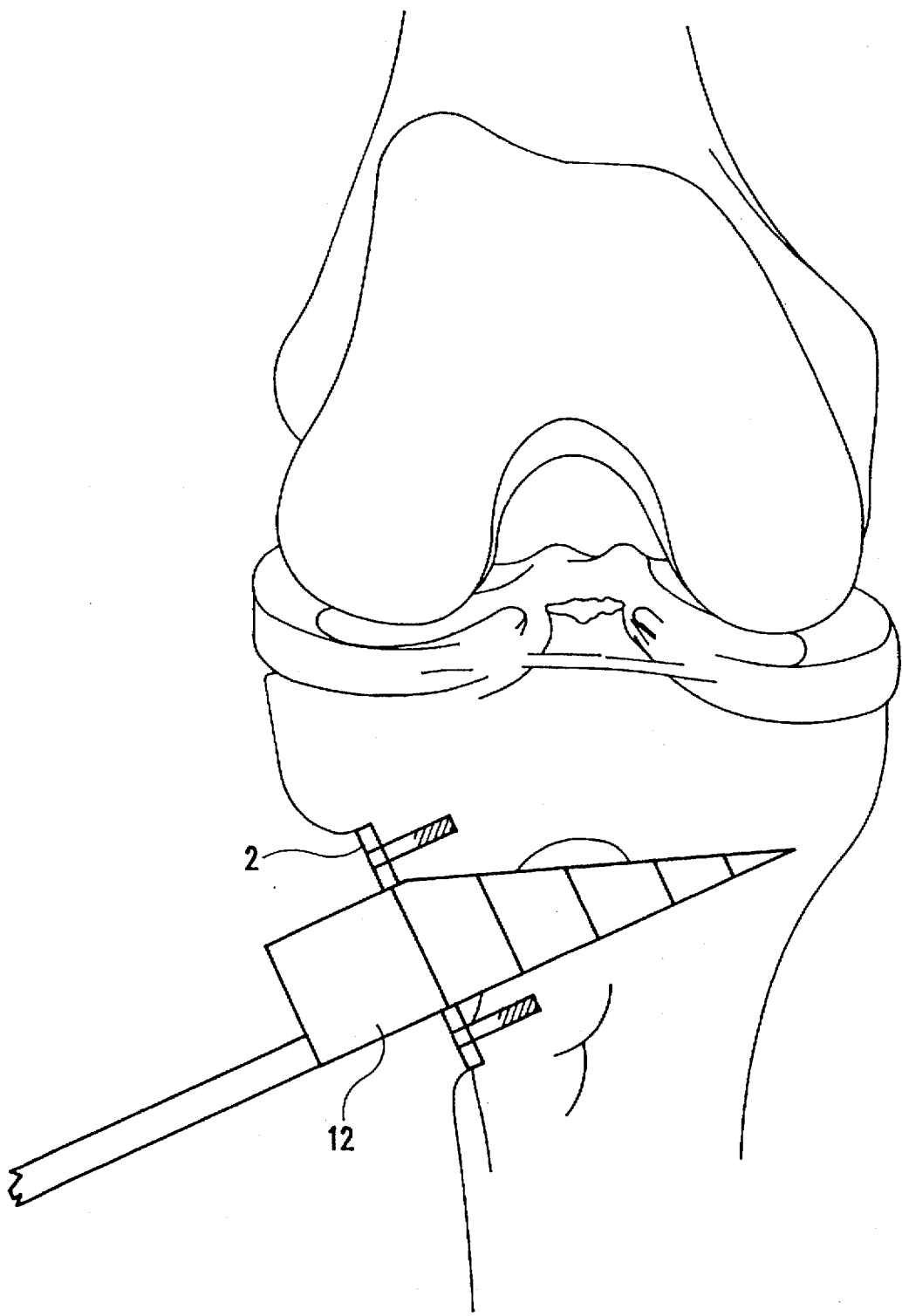
FIG. 8 is a schematic representation of the bone plate insertion step in the method of the present invention.

6. Referring to FIG. 8, bone plate 2, of appropriate thickness, is then placed in the opening of the fork with one screw hole 4 above the osteotomy site, and the other below. The plate is then secured to the bone with bone screws, using standard AO technique. Once the plate is positioned and the bone graft is inserted, fixation is obtained by inserting a cancellous screw in the proximal hole and a cortical screw in the distal hole.

Figure 9:
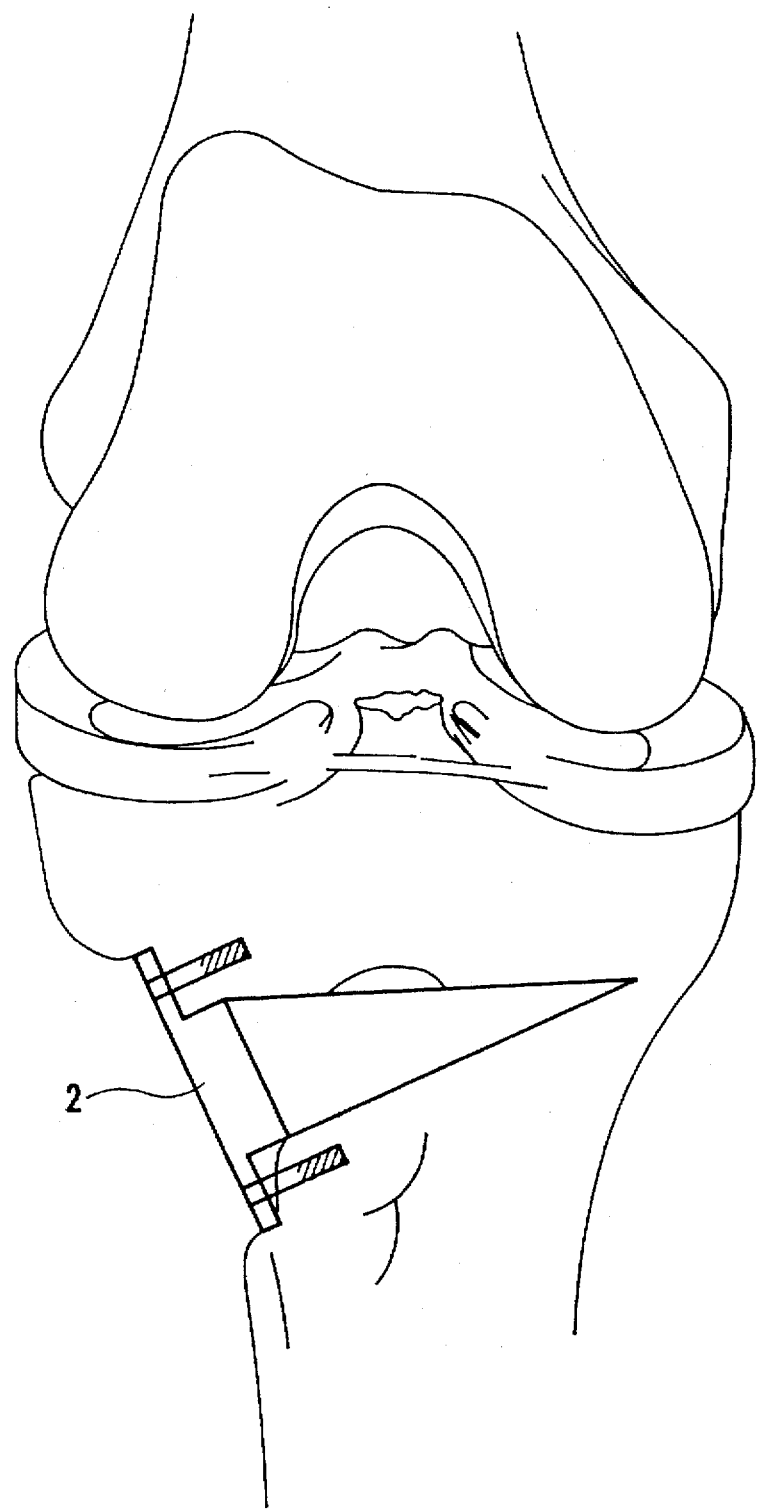
FIG. 9 is a schematic representation of the wedge tool removal step in the method of the present invention.

7. The forked wedge tool is then removed and autologous bone is packed into the defect. See FIG. 9. If the gap in the corrected tibia is 7.5 mm or less, autograft bone is taken from the tibia. If the gap is wider than 7.5 mm, the bone graft is taken from the iliac crest. This provides a good osteosynthesis and a correction that does not reduce in time.

8. The wound is closed in the usual manner. The medial collateral ligament is then repaired and the skin incision is closed.

Limited weight bearing for six weeks, or until adequate callous formation can be determined, is advised.

Post-operative Rehabilitation

The patient is placed in either a cast or full leg brace (non-weight bearing) based on surgeon preference and rehab is carried out for about 30 days with patient progress determined by bone-healing times indicated by progressive x-ray follow up.

A combination ACL reconstruction and open wedge HTO is not contraindicated and may be performed when necessary. The arthroscopy is performed as previously described and the remnants of the ACL are completely resected followed by a standard notchplasty. Either a patellar tendon or semitendinosus autograft technique may be used. Positioning and fixation of the HTO plate is carried out more posterior in these cases to allow room for the tibial tunnel. Tibial tunnel creation can be carried out using a coring reamer as disclosed in allowed U.S. application Ser. No. 08/019,356 (the disclosure of which is herein incorporated by reference), and the bone core is used as osteotomy autograft material if not used to build a bone-hamstring construct. Interference screw fixation of the graft in the tibia can be performed, but placement of the screw should be made opposite the osteotomy incision line in the anterior medial tibia to prevent conflict with placement and fixation of the HTO plate. Rehab is as previously indicated with non-weight bearing for 30 days and range of motion as dictated by the ACL reconstruction.

The above-described technique and bone plate system can also be used to perform femoral osteotomy. Post-op rehab requires a minimum 45 days non-weight bearing in these cases, however.

The present invention is unique in that it uses a calibrated wedge to determine what size spacer is necessary to eliminate the previous deformity. No other known device uses spacers. Not only is the method easy to perform, but it more accurate than other known methods.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A system for performing opening wedge osteotomies in which a bone is resected so as to have an opening on one side governed by a bony hinge on the other side, the system comprising:

a plurality of bone plates, each bone plate having two ends, a width, a proximal side, and a distal side, the distal side having at least one projection with a length and a depth for insertion into the opening to prevent closure of the opening, the projection having opposed edges for engaging and propping open the bone, the plate extending toward the ends on either side of the projection for engaging an outer surface of the bone; and a tool having a distal end and a proximal end, the distal end of the tool including a wedge having two prongs, the two prongs being separated from each other by a distance greater than the width of the bone plates, the prongs of the wedge having a substantially linearly tapered thickness beginning at the distal end for wedging and holding open the resected bone and receiving between the prongs a selected bone plate for propping open the wedged open resected bone.

2. The system of claim 1, wherein the thickness of the wedge is calibrated in relation to the length of the projections.

3. The system of claim 1, wherein five bone plates are provided, and the length of the projection on each bone plate is 5 mm, 7.5 mm, 10 mm, 12.5 mm and 15 mm, respectively.

4. The system of claim 1, wherein each of the ends of the bone plates has a hole for receiving a bone screw.

5. The system of claim 1, wherein the depth of the projection is four millimeters.

6. The system of claim 1, wherein the wedge thickness tapers linearly.

7. The system of claim 1, wherein the plate is curved.

8. The system of claim 7, wherein the curve is formed distally.

9. The system of claim 1, wherein the proximal end of the tool includes a handle.

10. The system of claim 1, wherein the proximal end and the distal end have a common longitudinal axis.

11. A system for correcting a deformity by performing an open-wedge osteotomy, the bone being resected to have an opening on one side and a bony hinge on the other, the system comprising:

a tool for wedging apart the bone on the open side of the resected bone, the tool having a distal end and a proximal end, the distal end including at least two prongs separated by a distance, each prong being in the form of a wedge having a substantially-linearly tapered thickness beginning from the distal end; and a plurality of bone plates for propping open the wedged apart bone on the open side of the resected site, each bone plate having projections projecting distally into the opening for preventing closure of the open side of the resected site, and a width less than the distance between the prongs of the wedge, such that the bone plate fits between the two prongs of the tool for insertion of the projections into a resected site wedged open by the tool, and extensions on either side of the projections for engaging an outer surface of the bone.

12. A system for correcting a deformity by performing an osteotomy in a bone at an osteotomy site, the system comprising:

means for wedging bone open at a resected site, the resected site having an open side and a hinged side, the means for wedging bone having a distal end and a proximal end, and including two prongs being separated by a distance, the prongs being in the form of a wedge having a substantially-linearly tapered thickness beginning at the distal end; and means for preventing closure of the open side of the resected site wedged open by the means for wedging, each means for preventing closure having projections for insertion into the open side of the resected site, the width of each bone plate being less than the distance separating the prongs, such that the bone plate fits between the two prongs of the tool for insertion of the projections into a resected site wedged open by the wedge means.

* * * * *